United States Patent
Saha et al.

(10) Patent No.: US 11,160,780 B2
(45) Date of Patent: Nov. 2, 2021

(54) PHARMACEUTICAL COMPOSITION OF IVERMECTIN AND PROCESS FOR PREPARATION THEREOF

(71) Applicants: AUROBINDO PHARMA LIMITED, Hitech (IN); Biswajit Saha, Hitech (IN); Nilendu Sen, Hitech (IN); Meenakshisunderam Sivakumaran, Hitech (IN)

(72) Inventors: Biswajit Saha, Hitech (IN); Nilendu Sen, Hitech (IN); Sivakumaran Meenakshisunderam, Hitech (IN)

(73) Assignee: Aurobindo Pharma Ltd., Hydevabad (IN)

(*) Notice: Subject to any disclaimer, the term of this patent is extended or adjusted under 35 U.S.C. 154(b) by 0 days.

(21) Appl. No.: 16/338,593

(22) PCT Filed: Sep. 27, 2017

(86) PCT No.: PCT/IB2017/055885
§ 371 (c)(1),
(2) Date: Apr. 1, 2019

(87) PCT Pub. No.: WO2018/060870
PCT Pub. Date: Apr. 5, 2018

(65) Prior Publication Data
US 2019/0282538 A1 Sep. 19, 2019

(30) Foreign Application Priority Data

Sep. 30, 2016 (IN) .............................. 201641033510

(51) Int. Cl.
| A61K 31/35 | (2006.01) |
| A61K 31/7048 | (2006.01) |
| A61P 17/00 | (2006.01) |
| A61K 9/00 | (2006.01) |
| A61K 9/107 | (2006.01) |
| A61K 47/32 | (2006.01) |

(52) U.S. Cl.
CPC ............ *A61K 31/35* (2013.01); *A61K 9/0014* (2013.01); *A61K 9/107* (2013.01); *A61K 31/7048* (2013.01); *A61K 47/32* (2013.01); *A61P 17/00* (2018.01)

(58) Field of Classification Search
None
See application file for complete search history.

(56) References Cited

U.S. PATENT DOCUMENTS

| 5,853,740 | A | * | 12/1998 | Lu | .......................... | A61K 9/113 |
| | | | | | | 424/400 |
| 6,584,988 | B1 | * | 7/2003 | Lazarowitz | ............. | B09C 1/002 |
| | | | | | | 134/25.1 |
| 2006/0100165 | A1 | * | 5/2006 | Manetta | ............... | A61K 9/0014 |
| | | | | | | 514/28 |
| 2009/0136574 | A1 | * | 5/2009 | Diaz-Astruc | ........ | A61K 9/0014 |
| | | | | | | 424/484 |
| 2015/0011489 | A1 | * | 1/2015 | Jacovella | ........... | A61K 31/7048 |
| | | | | | | 514/30 |
| 2015/0190327 | A1 | * | 7/2015 | Djedour | ............... | A61K 9/0014 |
| | | | | | | 424/490 |
| 2017/0049748 | A1 | * | 2/2017 | Murthy | ................ | A61K 31/415 |

OTHER PUBLICATIONS

Yazadanian et al ("The Effect of Diethylene Glycol Monoethyl Ether as a Vehicle for Topical Delivery of Ivermectin", Veterinary Research Communications, vol. 19 (1995), p. 309-319) (Year: 1995).*

* cited by examiner

*Primary Examiner* — Sin J Lee
(74) *Attorney, Agent, or Firm* — Jay R Akhave; Patent Science LLC

(57) ABSTRACT

The invention relates to a topical pharmaceutical composition comprising effective amount of ivermectin as an active agent, process of preparation thereof and method of treating dermatological conditions such as inflammatory lesions of rosacea, common acne, seborrheic dermatitis, perioral dermatitis, acne form rashes, and the like.

18 Claims, No Drawings

PHARMACEUTICAL COMPOSITION OF IVERMECTIN AND PROCESS FOR PREPARATION THEREOF

FIELD OF THE INVENTION

The present invention relates to pharmaceutical composition comprising ivermectin as an active agent, process of preparation thereof and method of using the same.

The invention relates to a topical pharmaceutical composition comprising effective amount of ivermectin as an active agent and process of preparation thereof.

The invention relates to method of treating one or more dermatological conditions such as inflammatory lesions of rosacea, common acne, seborrheic dermatitis, perioral dermatitis, acneform rashes and the like, by applying topical pharmaceutical composition of ivermectin onto the affected skin area of a subject in need of such treatment.

BACKGROUND OF THE INVENTION

Dermatological conditions are associated with increased sensitivity of the skin. Dermatosis is a term that refers to diseases of the integumentary system and it includes everything on the surface of the body: skin, nails, and hair. Rosacea is an inflammatory dermatosis that affects the central part of the face and is characterized, by reddening of the face, dryness of the skin, hot flashes and facial erythemia. Rosacea develops in adults from the ages of 30 to 50 and it more frequently affects women.

Formerly, rosacea is known as acne rosacea and the aetiology of rosacea is still not clearly understood, the most common hypothesis is based on the characteristic presence of the parasite *Demodex folliculorum* in the case of patients suffering from rosacea but this organism is not present in common acne.

Conventionally, rosacea is treated orally or topically with various therapeutic agents such as antibiotics it includes tetracyclines, erythromycin, clindamycin or metronidazole, but also with vitamin A, salicylic acid, anti-fungal agents, steroids, anti-infectious agents such as benzoyl peroxide, with isotretinoin or with azelaic acid. Ivermectin is an anti-parasitic drug derivative from the macrocyclic lactones or avermectin family approved for human use for treatment and chemoprophylaxis of onchocerciasis and strongyloidiasis since 1996 in the USA.

Ivermectin is a mixture of two compounds belonging to the avermectin class, 5-O-demethyl-22, 23-dihydroavermectin A1a and 5-O-demethyl-22, 23-dihydroavermectin A1b. They are also known under the name 22, 23-dihydroavermectin B1a and 22, 23-dihydroavermectin B1b and have following structural formula:

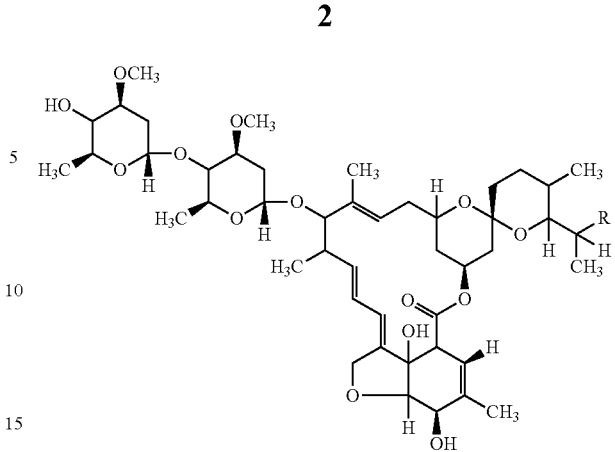

Component B1a: R=$C_2H_5$, Component B1b: R=$CH_3$.

Ivermectin is known in the prior art for its anti-parasitic and anthelmintic properties. U.S. Pat. No. 5,952,372 describes a method of treating rosacea by orally-administering or topically-applying ivermectin.

Ivermectin Tablets 3 mg & 6 mg was approved in the USA since 1996 under the trade name Stromectol® by Merck Sharp And Dohme Corp. Ivermectin cream (Topical; 1% or 10 mg/1 gm) was approved in the USA on Dec. 19, 2014 for the treatment of inflammatory lesions of rosacea and currently sold under the trade name Soolantra® by Galderma Laboratories LP. The inactive ingredients of Soolantra® are: Carbomer copolymer type B, Cetyl alcohol, Citric acid monohydrate, Dimethicone, Edetate disodium, Glycerin, Isopropyl palmitate, Methylparaben, Oleyl alcohol, Phenoxyethanol, Polyoxyl 20 Cetostearyl ether, Propylene glycol, Propylparaben, Purified water, Sodium hydroxide, Sorbitan monostearate, and Stearyl alcohol.

U.S. Pat. No. 6,133,310 describes a method of treatment of acne rosacea by applying ivermectin in the form of lotion daily to an affected area.

WO 2004/093886 discloses the use of ivermectin for the treatment of dermatological conditions such as rosacea, acne vulgaris. WO 2004/093886 discloses stable pharmaceutical emulsions comprising novel surfactant-emulsifiers.

WO 2005/089806 discloses pharmaceutical composition of the avermectin family, in the form of a cream-gel comprising, in a physiologically acceptable medium, an oily phase dispersed in an aqueous phase by means of a non-surfactant polymeric emulsifier.

U.S. Pat. No. 8,362,069 describes a pharmaceutical/dermatological emulsion which comprises at least one fatty phase, at least one aqueous phase, at least one avermectin compound, and one or more other additives.

U.S. Pat. No. 8,287,891 describes a cosmetic/dermatological composition which comprises an inverse emulsion of a glycolic or aqueous/glycolic hydrophilic phase dispersed in a continuous lipophilic phase.

U.S. Pat. No. 8,563,524 describes that treatment using ivermection have drawbacks such as irritation and intolerance phenomena, especially when they are administered for a prolonged period. Therefore, U.S. Pat. No. 8,563,524 describes a pharmaceutical/dermatological topically applicable composition useful for the treatment of rosacea in the absence of irritation and intolerance, comprising anti-rosacea effective amounts of ivermectin and azelaic acid or salt thereof, and a gelling agent selected from the group consisting of acrylamide/sodium acryloyldimethyltaurate copolymer/isohexane/polysorbate 80 gelling agent. WO 2004/093886 and WO 2005/089806 describe emulsions comprising ivermectin.

Considering the chronic nature of rosacea, the ideal treatment requires prolonged use of ivermectin and thus there is a need for a development of composition that shows improved efficacy without any side effects or minimal side effects described in the prior art. The development of ivermectin compositions is not easy because ivermectin is a compound that is chemically unstable when it comes in contact with water.

Several attempts had been made in order to achieve stable topical creams (emulsions) of ivermectin:—
  a) EP 0,045,655 describes formation of micelles of surfactants which surround the ivermectin in order to protect the drug against water.
  b) WO 01/60380 and WO 97/26895 describe the use of aqueous miscible solvents, such as N-methyl-2-pyrrolidone.
  c) WO 2004/093886 describes use of amphiphilic Surfactant-emulsifiers for stabilizing the dispersions in order to increase the stability of the dispersion by decreasing the interface tension energy.
  d) WO 2005/089806 describes emulsions in the form of a cream-gel comprising, with the use of non-surfactant polymeric emulsifiers and oils.

The low solubility in water and the low compatibility with many excipients specifically with non-ionic emulsion excipients, made it increasingly difficult for preparing the pharmaceutical compositions containing ivermectin, requiring either the addition of a large number of additives to obtain stable compositions, which in turn has the effect of increasing the risk of allergies, or to be formulated with anhydrous excipients. Also the anhydrous compositions conventionally have the disadvantage of a greasy feel and therefore of an appearance that is not very cosmetic, which may be responsible for a decrease in patient compliance. In addition, by virtue of the low stability of ivermectin in water, the shelf life of aqueous compositions containing ivermectin is generally shorter than that of anhydrous compositions containing ivermectin.

There still remains a need to design pharmaceutical composition of ivermectin that are easy to formulate, have improved stability, reduced side effects but have the desired therapeutic effect. Inventors of the present invention have endeavored to develop such formulations that are also economical and commercially viable. The compositions of the present invention exhibit excellent stability, good tolerance on the skin and improved patient compliance particularly in the treatment of dermatological disorders or disease conditions.

SUMMARY OF THE INVENTION

An aspect of the invention relates to pharmaceutical composition comprising ivermectin as an active agent, process of preparation thereof and method of using the same.

An aspect of the invention relates to a topical pharmaceutical composition comprising effective amount of ivermectin as an active agent and process of preparation thereof.

An aspect of the invention provides a topical pharmaceutical composition comprising: a) about 0.1-5% w/w of an ivermectin; b) an oily phase comprising at least one surfactant emulsifier, c) an aqueous phase comprising gelling agent; d) optionally suitable pharmaceutically acceptable excipients.

An aspect of the invention provides a topical pharmaceutical composition comprising: a) about 0.1-5% w/w of an ivermectin; b) an oily phase comprising at least one surfactant emulsifier selected from polyethylene glycol ethers of fatty alcohol; c) an aqueous phase comprising gelling agent selected from alkyl acrylate crosspolymer, sodium acryloyldimethyl taurate copolymer or combinations thereof; d) optionally suitable pharmaceutically acceptable excipients.

An aspect of the invention provides a topical stable pharmaceutical composition comprising: a) about 0.1-5% w/w of an ivermectin; b) an oily phase comprising at least one surfactant emulsifier selected from 1.5-7% w/w of Polyethylene glycol ethers of oleyl or lauryl alcohol; c) an aqueous phase comprising 0.1-1.2% w/w gelling agent selected from alkyl acrylate crosspolymer (carbomer), or sodium acryloyldimethyl taurate copolymer (For example—Sepineo™ derm, Sepineo™ P 600 or Simulgel™ 600); d) optionally suitable pharmaceutically acceptable excipients.

An aspect of the invention provides a topical pharmaceutical composition comprising: a) about 0.1-5% w/w of an ivermectin; b) 1.5-7% w/w of Polyoxyl 20 cetosteryl alcohol; c) 0.1-1.2% w/w gelling agent selected from alkyl acrylate crosspolymer (carbomer), or sodium acryloyldimethyl taurate copolymer (For example—Sepineo™ derm, Sepineo™ P 600, Simulgel™ 600); d) diethyleneglycol monoethyl ether and e) optionally suitable pharmaceutically acceptable excipients.

An aspect of the invention provides a topical pharmaceutical composition of ivermectin comprising: a) about 0.1-5% w/w of an ivermectin; b) an oily phase comprising at least one solubilizer or permeation enhancer selected from 1.5-7% w/w of Polyoxyl 20 cetosteryl alcohol; c) an aqueous phase comprising 0.1-1.2% w/w gelling agent selected from alkyl acrylate crosspolymer (carbomer), or sodium acryloyldimethyl taurate copolymer (For example—Sepineo™ derm, Sepineo™ P 600 or Simulgel™ 600); d) optionally suitable pharmaceutically acceptable excipients.

An aspect of the invention provides a topical pharmaceutical composition comprising: a) about 1% ivermectin; b) 1.5-7% w/w of Polyoxyl 20 cetosteryl alcohol; c) 0.1-1.2% w/w gelling agent selected from alkyl acrylate crosspolymer (carbomer), or sodium acryloyldimethyl taurate copolymer (For example—Sepineo™ derm, Sepineo™ P 600 or Simulgel™ 600); d) diethyleneglycol monoethyl ether.

An aspect of the invention provides topical pharmaceutical composition comprising:
  a) an oily phase comprising at least one fatty substance;
  b) at least one emulsifier;
  c) ivermectin;
  d) one or more solvent (s) and/or penetrating agent(s);
  e) one or more gelling agents; and
  f) water.

An aspect of the invention provides a topical pharmaceutical composition comprising:
  a) an oily phase comprising fatty substances;
  b) at least one surfactant selected from polyethylene glycol ether of oleyl alcohol or lauryl alcohol;
  c) ivermectin;
  d) one or more solvent (s) and/or one or more penetrating agent(s) selected from propylene glycol, phenoxy ethanol and mixtures thereof;
  e) one or more gelling agents selected from acrylate alkyl acrylate crosspolymer (such as Carbomer™) or Hydroxyethyl Acrylate/Sodium Acryloyldimethyl Taurate Copolymer (such as Sepineo™ Derm), Acrylamide/Sodium acryloyldimethyl taurate copolymer/Isohexadecane & Polysorbate 80 (such as Sepineo™ P 600 or Simulgel™ 600) or mixture thereof;

f) water.

An aspect of the invention provides a topical pharmaceutical composition comprising:

a) an oily phase comprising fatty substances;

b) at least one emulsifier selected from polyethylene glycol ether of oleyl alcohol or lauryl alcohol in an amount of about 2-10% w/w based on the total weight of the pharmaceutical composition;

c) ivermectin in an amount of about 0.1-10% w/w based on the total weight of the pharmaceutical composition;

d) one or more solvent (s) and/or one or more penetrating agent(s) selected from propylene glycol, phenoxy ethanol and mixtures thereof;

e) one or more gelling agents selected from acrylate alkyl acrylate crosspolymer or Hydroxyethyl Acrylate/Sodium Acryloyldimethyl Taurate, Acrylamide/Sodium acryloyldimethyl taurate copolymer/Isohexadecane & Polysorbate 80 (such as Sepineo™ P 600 or Simulgel™ 600), or mixture thereof in an amount of about 0.1 to 10% w/w based on the total weight of the pharmaceutical composition;

f) water.

An aspect of the invention provides a topical pharmaceutical composition in the form of cream comprising:

a) about 1-10% w/w ivermectin;

b) about 0.2-5% w/w of acrylate alkyl acrylate crosspolymer or 0.5-5% w/w of Hydroxyethyl Acrylate/Sodium Acryloyldimethyl Taurate Copolymer or Acrylamide/Sodium acryloyldimethyl taurate copolymer/Isohexadecane & Polysorbate 80 or mixture thereof;

c) about 0.4-5% w/w dimethicone;

d) about 2-10% w/w esters of sebacic acid or dimethyl isosorbide;

e) about 3-30% w/w Polyethylene glycol ethers of oleyl alcohol (Oleth 20);

f) about 2-20% w/w Polyethylene glycol ethers of oleyl alcohol (Oleth 2);

g) water, and h) optionally one or more additional pharmaceutically acceptable ingredients.

An aspect of the invention provides a topical pharmaceutical composition in the form of cream comprising:

a) 1% w/w Ivermectin;

b) 0.2-1.2% w/w of Carbomer co-polymer or Hydroxyethyl Acrylate/Sodium Acryloyldimethyl Taurate Copolymer or Acrylamide/Sodium acryloyldimethyl taurate copolymer/Isohexadecane & Polysorbate 80 or mixture thereof;

c) 0.5% w/w of Dimethicone;

d) 4% w/w of diethyl sebacate or dimethyl isosorbide;

e) 2-4% w/w of Polyethylene glycol ethers of lauryl alcohol (Laureth 23) or oleyl alcohol (Oleth 20)

f) 2-4% w/w of polyethylene glycol ethers of lauryl alcohol (Laureth 4) or oleyl alcohol (Oleth 2)

g) water, and h) optionally suitable pharmaceutically acceptable ingredients.

An aspect of the invention provides a topical pharmaceutical composition in the form of cream comprising:

a) Ivermectin;

b) 0.1-1.2% w/w of Carbomer co-polymer or Hydroxyethyl Acrylate/Sodium Acryloyldimethyl Taurate Copolymer or Acrylamide/Sodium acryloyldimethyl taurate copolymer/Isohexadecane & Polysorbate 80 or mixture thereof;

c) 0.5% w/w of Dimethicone;

d) 4% w/w of isopropyl palmitate;

e) 2-6% w/w of Polyethylene glycol ethers of lauryl or oleyl alcohol f) water, and g) optionally suitable pharmaceutically acceptable ingredients.

Another aspect of the invention provides the process for the preparation of topical pharmaceutical composition comprising:

a) Preparing the aqueous phase;

b) Preparing the oil phase;

c) Adding ivermectin in to a suitable pharmaceutically acceptable excipients or solvent system to form active phase;

d) Adding oil phase to aqueous phase and homogenizing;

e) Adding the active phase of step-c to step-d to obtain a suitable dosage form.

Surprisingly, the topical pharmaceutical composition comprising ivermectin provides excellent storage stability over a period of six months. The pH of the said topical composition is 4.5-7.5 and viscosity is in the range of 0.1-5 poise. More preferably the pH of the said topical composition is 5.5-7.0 and viscosity is in the range of 0.1-2 poise An aspect of the invention relates to method to treating one or more dermatological conditions such as inflammatory lesions of rosacea, common acne, seborrheic dermatitis, perioral dermatitis, acneform rashes and the like, by applying topical pharmaceutical composition of ivermectin onto the affected skin area of a subject in need of such treatment.

DETAILED DESCRIPTION OF THE INVENTION

The term "therapeutically effective amount" is defined to mean the amount or quantity of the active drug (e.g. ivermectin), which is sufficient to elicit an appreciable biological response when administered/treated to the patient.

The term "excipient" means a pharmacologically inactive component such as a solvent, diluent, disintegrant, gelling agent, surfactant, carrier, or the like. The excipients that are useful in preparing a pharmaceutical composition are generally safe, non-toxic and are acceptable for veterinary as well as human pharmaceutical use. Reference to an excipient includes both one and more than one such excipient.

The term "composition" or "pharmaceutical composition" or "dosage form" or "topical pharmaceutical composition" as used herein synonymously include dosage forms such as cream, ointment, emulsion, gel, spray, foam, lotion and shampoo, and the like.

The term "pharmaceutically acceptable" means molecular entities and compositions that are of sufficient purity and quality for use in the formulation of a composition or medicament of the present invention.

In an embodiment, the invention provides pharmaceutical composition comprising ivermectin as an active agent, process of preparation thereof and method of using the same.

In an embodiment, the invention provides a topical pharmaceutical composition comprising effective amount of ivermectin as an active agent and process of preparation thereof.

"Pharmaceutically acceptable excipient(s)" are components that are added to the pharmaceutical formulation other than the active ingredient ivermectin. Excipients may be added to facilitate manufacture, enhance stability, enhance product characteristics, enhance skin penetration, enhance patient acceptability etc. Pharmaceutically acceptable excipient(s) includes, but not limited to, one or more filler, gelling agent, surfactant, humectant, pH modifier, chelating agent, acidifying agent, viscosity enhance, solvent, vehicle, oily vehicle, color, preservative, suspending agent, dispersing agent, and any other excipient known to the art for making pharmaceutical formulation. According to the present invention a particular excipient may perform multiple roles in the pharmaceutical composition, for example, it can act both as a preservative and, or as a pH modifier.

In an embodiment, the invention provides a topical pharmaceutical composition comprising: a) about 0.1-5% w/w of an ivermectin; b) an oily phase comprising at least one surfactant emulsifier, c) an aqueous phase comprising gelling agent; d) optionally suitable pharmaceutically acceptable excipients.

In an embodiment, the invention provides a topical pharmaceutical composition comprising: a) about 0.1-5% w/w of an ivermectin; b) an oily phase comprising at least one surfactant emulsifier selected from polyethylene glycol ethers of fatty alcohol; c) an aqueous phase comprising gelling agent selected from alkyl acrylate crosspolymer, sodium acryloyldimethyl taurate copolymer or combinations thereof; d) optionally suitable pharmaceutically acceptable excipients.

In an embodiment, the invention provides a topical stable pharmaceutical composition comprising: a) about 0.1-5% w/w of an ivermectin; b) an oily phase comprising at least one surfactant emulsifier selected from 1.5-7% w/w of Polyethylene glycol ethers of oleyl or lauryl alcohol; c) an aqueous phase comprising 0.1-1.2% w/w gelling agent selected from alkyl acrylate crosspolymer (carbomer), or sodium acryloyldimethyl taurate copolymer (For example— Sepineo™ derm, Sepineo™ P 600 or Simulgel™ 600); d) optionally suitable pharmaceutically acceptable excipients.

In an embodiment, the invention provides a topical pharmaceutical composition comprising: a) about 0.1-5% w/w of an ivermectin; b) 1.5-7% w/w of Polyoxyl 20 cetosteryl alcohol; c) 0.1-1.2% w/w gelling agent selected from alkyl acrylate crosspolymer (carbomer), or sodium acryloyldimethyl taurate copolymer (For example—Sepineo™ derm, Sepineo™ P 600 or Simulgel™ 600); d) diethyleneglycol monoethyl ether and e) optionally suitable pharmaceutically acceptable excipients.

In an embodiment, the invention provides a topical pharmaceutical composition of ivermectin comprising: a) about 0.1-5% w/w of an ivermectin; b) an oily phase comprising at least one solubilizer or permeation enhancer selected from 1.5-7% w/w of Polyoxyl 20 cetosteryl alcohol; c) an aqueous phase comprising 0.1-1.2% w/w gelling agent selected from alkyl acrylate crosspolymer (carbomer), or sodium acryloyldimethyl taurate copolymer (For example—Sepineo™ derm, Sepineo™ P 600 or Simulgel™ 600); d) optionally suitable pharmaceutically acceptable excipients.

In an embodiment, the invention provides a topical pharmaceutical composition comprising: a) about 1% ivermectin; b) 1.5-7% w/w of Polyoxyl 20 cetosteryl alcohol; c) 0.1-1.2% w/w gelling agent selected from alkyl acrylate crosspolymer (carbomer), or sodium acryloyldimethyl taurate copolymer (For example—Sepineo™ derm, Sepineo™ P 600 or Simulgel™ 600); d) diethyleneglycol monoethyl ether.

In an embodiment, the invention provides a topical pharmaceutical composition comprising: a) about 0.1-5% w/w of an ivermectin; b) an oily phase comprising at least one surfactant emulsifier, c) an aqueous phase comprising gelling agent; d) optionally suitable pharmaceutically acceptable excipients, wherein said composition have the pH 4.5-7.5 and viscosity is in the range of 0.1-5 poise, more preferably the pH is 5.5-7.0 and viscosity is in the range of 0.1-2 poise and said composition is stable over a period of 6 months when stored at 40° C. and at 75% Relative humidity In an embodiment, the invention provides a topical pharmaceutical composition comprising:
a) an oily phase comprising fatty substances;
b) emulsifier selected from polyethylene glycol ether of oleyl alcohol or lauryl alcohol in an amount of about 2-10% w/w based on the total weight of the pharmaceutical composition;
c) ivermectin in an amount of about 0.1-10% w/w based on the total weight of the pharmaceutical composition;
d) one or more solvent (s) and/or one or more penetrating agent (s) selected from propylene glycol, phenoxy ethanol and mixtures thereof;
e) one or more gelling agents selected from acrylate alkyl acrylate crosspolymer (carbomer) or Hydroxyethyl Acrylate/Sodium Acryloyldimethyl Taurate Copolymer (Sepineo™ Derm) or Acrylamide/Sodium acryloyldimethyl taurate copolymer/Isohexadecane & Polysorbate 80 (such as Sepineo™ P 600 or Simulgel™ 600) or mixture thereof in an amount of about 0.1 to 10% w/w based on the total weight of the pharmaceutical composition;
f) water.

In an embodiment, the invention provides a topical pharmaceutical composition in the form of cream comprising:
a) about 1-10% w/w ivermectin;
b) about 0.2-5% w/w of acrylate alkyl acrylate crosspolymer (carbomer) or 0.8-5% w/w of Hydroxyethyl Acrylate/Sodium Acryloyldimethyl Taurate Copolymer (Sepineo™ Derm) or Acrylamide/Sodium acryloyldimethyl taurate copolymer/Isohexadecane & Polysorbate 80 (such as Sepineo™ P 600 or Simulgel™ 600);
c) about 0.5-5% w/w dimethicone;
d) about 2-10% w/w esters of sebacic acid or dimethyl isosorbide;
e) about 3-30% w/w Polyethylene glycol ethers of oleyl alcohol (Oleth 20);
f) about 2-20% w/w Polyethylene glycol ethers of oleyl alcohol (Oleth 2);
g) water, and
h) optionally one or more additional pharmaceutically acceptable ingredients.

In an embodiment, the invention provides a topical pharmaceutical composition in the form of cream comprising:
a) 1% w/w Ivermectin;
b) 0.2% w/w of Carbomer co-polymer or 0.80-1.0% w/w of Hydroxyethyl Acrylate/Sodium AcryloylDimethyl Taurate Copolymer (Sepineo™ Derm) or Acrylamide/Sodium acryloyldimethyl taurate copolymer/Isohexadecane & Polysorbate 80 (such as Sepineo™ P 600 or Simulgel™ 600);
c) 0.5% w/w of Dimethicone;
d) 4% w/w of diethyl sebacate or dimethyl isosorbide;
e) 3-4% w/w of Polyethylene glycol ethers of lauryl alcohol (Laureth 23) or oleyl alcohol (Oleth 20)
f) 2-3% w/w of Polyethylene glycol ethers of lauryl alcohol (Laureth 4) or oleyl alcohol (Oleth 2)
g) water, and
h) optionally suitable pharmaceutically acceptable ingredients.

In an embodiment, the invention provides a topical pharmaceutical composition in the form of cream comprising:
a) 1% w/w Ivermectin;
b) 0.1-1.2% w/w of Carbomer co-polymer or Hydroxyethyl Acrylate/Sodium Acryloyldimethyl Taurate Copolymer (Sepineo™ Derm) or Acrylamide/Sodium acryloyldimethyl taurate copolymer/Isohexadecane & Polysorbate 80 (such as Sepineo™ P 600 or Simulgel™ 600);
  c) 0.5% w/w of Dimethicone;
  d) 4% w/w of isopropyl palmitate;
  e) 2-6% w/w of Polyethylene glycol ethers of lauryl or oleyl alcohol
  f) water, and
  g) optionally suitable pharmaceutically acceptable ingredients.

In one of the particular embodiments of the invention provides a process for the preparation of topical pharmaceutical composition of ivermectin, comprises the following steps:
  a) Preparation of aqueous phase comprising glycerin, citric acid;
  b) Preparation of oil phase comprising stearyl alcohol, oleyl alcohol, cetyl alcohol or combinations thereof;
  c) Mixing of ivermectin in to suitable solvent to form active phase;
  d) Addition of oil phase to aqueous phase and homogenization;
  e) Addition of active phase in to step-d to form suitable dosage form.

The oily phase of the composition according to the invention may comprise, for example, cetyl alcohol, stearyl alcohol, oleyl alcohol, oils such as vegetable, mineral, animal or synthetic oils, silicone oils, or other substances, and mixtures thereof. Other examples include paraffin oils of various viscosities, sweet almond oil, palm oil, soybean oil, sesame oil and sunflower oil, lanolin, squalene, fish oil, cetearyl isononanoate, diisopropyl adipate, isopropyl palmitate, or caprylic capric triglyceride, dimethicone, fatty substances such as stearic acid, fatty alcohols cetostearyl alcohol and cetyl alcohol, or derivatives thereof, waxes such as beeswax, carnauba wax or candelilla wax, and also gums, in particular silicone gums and a like. The ingredients of the oily phase may be selected by those skilled in the art in order to prepare a composition having the desired properties.

The oily phase of the emulsion according to the invention may be present at a content of from 8 to 40% by weight relative to the total weight of the composition, and preferably from 10 to 25% by weight and more preferably from 14 to 20% by weight.

The compositions of the invention contain from 0.5 to 10%, and preferably from 2 to 6%, of a solvent and/or penetrating agent or penetration enhancers. Penetration enhancers are the substances used to increase permeation of skin mucosa. Penetration enhancer increases the absorption of penetrant through the skin which is also known as absorption promoter or absorption enhancers. Penetration enhancers used to increase the permeability of drug through skin. Suitable penetration enhancers according to the present invention can be any solvent in which the binder is soluble or dispersible and is selected from, but not limited to, glycerol, propylene glycol, isopropyl alcohol, ethanol, purified water, acetone, methylene chloride and the like either alone or mixtures thereof. Examples of a solvent and/or penetrating agent for the ivermectin active agent, will preferably be made of phenoxyethanol, propylene glycol, alcohols such as ethanol, isopropanol, isopropyl palmitate, butanol, N-methyl-2-pyrrolidone or DMSO, diethylene glycol monoethyl ether, polysorbate 80, esters of sebacic acid, diethyl sebacate, dimethyl isosorbide and mixtures thereof.

Suitable stabilizers or pH modifying agents used in the composition may be selected from carboxylic acids, and other types of compounds, are well known in the art. For example, include metal salts such as alkali metal salts, e. g. sodium or potassium salts of organic acids such as acetic acid, oxalic acid, malefic acid, tartaric acid, citric acid, succinic acid or malonic acid alone or in combination thereof or in combination with Ethylene Diaminetetraacetic acid (EDTA). Further suitable pH modifying agents include inorganic alkali hydroxides such as sodium hydroxide, potassium hydroxide and a like, inorganic base such as bicarbonates, carbonates, organic base such as diethylamine, ethanolamine, diethanolamine, triethanolamine, tromethamine, N-methylglucamine, and the like. Further, the pH adjusting agent can also be a buffer and suitable buffers include citrate/citric acid buffers, acetate/acetic acid buffers, phosphate/phosphoric acid buffers, formate/formic acid buffers, propionate/propionic acid buffers, lactate/lactic acid buffers, carbonate/carbonic acid buffers, ammonium/ammonia buffers, and the like.

Chelating agents which can be used to form a stable pharmaceutical compositions and dosage forms of the invention include, but are not limited to, ethylene Diaminetetraacetic acid (EDTA), EDTA disodium, calcium disodium edetate, EDTA trisodium, albumin, Transferrin, Desferoxamine, desferal, desferoxamine mesylate, EDTA tetrasodium and EDTA dipotassium, Sodium metasilicate alone or combinations of any of these or with citric acid.

Preservatives which can be used to form pharmaceutical compositions and dosage forms of the invention include, but are not limited to, methylparaben, ethylparaben and propylparaben, imidazolidinyl urea, diazolidinyl urea, phenoxyethanol, alkonium chlorides including benzalkonium chlorides. In other embodiments, suitable preservatives for the compositions of the invention include: benzalkonium chloride, purite, peroxides, perborates, thimerosal, chlorobutanol, methyl paraben, propyl paraben, phenylethyl alcohol, edetate disodium, sorbic acid, or other agents known to those skilled in the art preservatives may be employed at a level of from 0.004% to 0.2% w/w of the composition.

The compositions according to the invention advantageously comprise up to 14% by weight of suitable emulsifier or surfactant-emulsifier, preferably from 2 to 10% by weight, and more particularly from 3 to 6% by weight, relative to the total weight of the composition. Surfactants are compound which are capable of improving the wetting of the drug and/or enhancing the dissolution. The surfactant can be selected from hydrophilic surfactant or lipophilic surfactant or mixtures thereof. The surfactant can be anionic, nonionic, cationic, and/or zwitterionic surfactant. Surfactants according to the present invention are selected from, but not limited to, polyoxyethylenealkylaryl ethers such as polyoxyethylene lauryl ether (laureth-23, laureth-4), polyoxyethylenecetyl ether, polyoxyethylenestearyl ether; polyoxyethylene oleyl ether (oleth-20, oleth-2), polyethylene glycol (PEG) fatty acid esters such as PEG monolaurate, PEG dilaurate, PEG distearate, PEG dioleate; polyoxyethylenesorbitan fatty acid ester such as polysorbate 40, polysorbate 60, polysorbate 80; sorbitan fatty acid mono esters such as sorbitanmonolaurate, sorbitan monostearate, sorbitanmonooleate, sorbitansesquioleate, polyoxyl 20 cetostearyl ether, sorbitantrioleate, polyoxyethylene castor oil derivates such as polyoxyl castor oil, polyoxyl hydrogenated castor oil, sodium lauryl sulphate and the like used either alone or in combination thereof.

The compositions according to the invention may also comprise aqueous phase gelling compounds ranging from 0.1 to 3% by weight relative to the total weight of the composition. Preferably the compositions of the invention preferentially contain from 0.1 to 3%, and preferably from 1.0 to 3%, of gelling agent. Among the gelling agents which can be used in the composition according to the invention, may be made of carboxyvinyl polymers (such as carbomers), by way of nonlimiting examples, of carbomer, Carbopol 981, Carbopol ETD 2020, Carbopol 980, Carbopol Ultrez 10 NF and Pemulen TR1, Hydroxyethyl Acrylate/ Sodium Acryloyldimethyl Taurate Copolymer (such as Sepineo™ Derm), Acrylamide/Sodium acryloyldimethyl taurate copolymer/Isohexadecane & Polysorbate 80 (such as Sepineo™ P 600 or Simulgel™ 600). As aqueous phase gelling agents, mention may also be made of cellulose derivatives such as, for example, hydroxypropylmethylcellulose or hydroxyethylcellulose; xanthan gums, aluminum/magnesium silicates such as Veegum K or Veegum Ultra, guar gums and the like, polyacrylamides such as the mixture polyacrylamide/C13-14 isoparaffin/laureth-7, or the mixture acrylamide, AMPS copolymer dispersion 40%/isohexadecane, or the family of modified starches such as structure Solanace or mixtures thereof.

In an embodiment, the composition of the invention may additionally comprise of a colorant in order to produce a desirable color. Colors known to be 'FD&C' certified may be used to provide coloring to the product and are within the purview of the present invention. Suitable colorants include natural colorants i.e., pigments and dyes obtained from mineral, plant, and animal sources. Examples of natural colorants include red ferric oxide, yellow ferric oxide, annattenes, alizarin, indigo, rutin, quercetin, and the like. Preferred colorants are food colorants in the 'GRAS' (Generally Regarded as Safe) category.

It is also desirable that the compositions are chemically stable and protected from degradation either by oxidation, hydrolysis, isomerisation, photolysis, polymerization, or any other method of degradation. The degradation may be as a result of mixing with excipients or by any other method, could lead to a change in pharmacokinetic parameters and could also lead to toxicity. Chemical stability can be measured by a suitable, stability indicating chromatographic method for determining degradation products (see Aulton Me., Pharmaceutics—The Science of Dosage Form Design, 2.sup.nd Edition, 2002, Churchill Livingstone).

The composition of the invention can be packed into suitable containers such as bottle, tube, pouch, or suitable container.

In an embodiment, the invention provides method to treating one or more dermatological conditions such as inflammatory lesions of rosacea, common acne, seborrheic dermatitis, perioral dermatitis, acneform rashes and the like, by applying topical pharmaceutical composition of ivermectin onto the affected skin area of a subject in need of such treatment.

The following examples serve to illustrate the embodiments of the invention. However, they do not intend to limit the scope of the invention. It is obvious to those skilled in the art to find out the composition for other dosage forms and substitute the equivalent excipients as described in this specification or with the one known to the industry.

Example 1

| No | Ingredients | 1A (% w/w) | 1B (% w/w) | 1C (% w/w) | 1D (% w/w) |
|---|---|---|---|---|---|
| 1 | Ivermectin | 1.0 | 1.0 | 1.0 | 1.0 |
| 2 | Propylene Glycol | 2.0 | 2.0 | 2.0 | 2.0 |
| 3 | Phenoxyethanol | 1.0 | 1.0 | 1.0 | 1.0 |
| 4 | Glycerol | 4.0 | 4.0 | 4.0 | 4.0 |
| 5 | Acrylate alkyl acrylate crosspolymer (Carbomer) | 0.20 | — | 0.20 | — |
| 6 | Hydroxyethyl Acrylate/Sodium Dimethyl Acryloyl Taurate Copolymer (Sepineo Derm ™) | — | 0.80 | — | 0.80 |
| 7 | Methylparaben | 0.20 | 0.20 | 0.20 | 0.20 |
| 8 | Disodium EDTA | 0.05 | 0.05 | 0.05 | 0.05 |
| 9 | Citric acid monohydrate | 0.05 | 0.05 | 0.05 | 0.05 |
| 10 | Dimethicone 200 20 cs | 0.50 | 0.50 | 0.50 | 0.50 |
| 11 | Diethyl sebacate/Dimethyl isosorbide | 4.0 | 4.0 | 4.0 | 4.0 |
| 12 | Cetyl alcohol | 3.50 | 3.50 | 3.50 | 3.50 |
| 13 | Stearyl alcohol | 2.50 | 2.50 | 2.50 | 2.50 |
| 14 | Oleyl alcohol | 2.0 | 2.0 | 2.0 | 2.0 |
| 15 | Polyethylene glycol ethers of oleyl alcohol (Oleth 20) | 3.0 | 3.0 | — | — |
| 16 | Polyethylene glycol ethers of oleyl alcohol (Oleth 2) | 2.0 | 2.0 | — | — |
| 17 | Polyethylene glycol ethers of lauryl alcohol (Laureth 23) | — | — | 3.0 | 3.0 |
| 18 | Polyethylene glycol ethers of lauryl alcohol (Laureth 4) | — | — | 2.0 | 2.0 |
| 19 | Propylparaben | 0.10 | 0.10 | 0.10 | 0.10 |
| 20 | 10% sodium Hydroxide | q.s. pH | q.s. pH | q.s. pH | q.s. pH |
| 21 | Purified water | q.s. | q.s. | q.s. | q.s. |
|  | Total | 100.00 |  | 100.00 | 100.00 | q.s.: Quantity sufficient

Manufacturing Process:
Preparation of Aqueous Phase:
i. Weighed and transferred batch quantity of purified water in SS container. A part quantity of purified water was kept a side for rinsing. Glycerin was added to purified water under stirring and heated to 60° to 70° C. Disodium EDTA, Citric acid, Methyl paraben and Dimethicone were added to it under stirring. ii. Carbomer copolymer (Pemulin TR1) or Hydroxyethyl Acrylate/Sodium AcryloylDimethyl Taurate Copolymer (Sepineo™ Derm) or Acrylamide/Sodium acryloyldimethyl taurate copolymer/Isohexadecane & Polysorbate 80 (such as Sepineo™ P 600 or Simulgel™ 600 or mixture thereof) was added to step-i under continuous stirring and mixed well to form clear aqueous phase.

Preparation of Oil Phase:

iii. The batch quantities of Cetyl alcohol, Stearyl alcohol, Oleyl alcohol, Oleth 20, Oleath 2, or Laureth 4, Laureth 23 as per composition mentioned in table, Propylparaben and Diethyl Sebacate/dimethyl isosorbide were weighed and transferred into another SS vessel. The mixture was heated to 60° to 70° C. and mixed well under slow anchor stirring.

Preparation of Drug Phase:

iv. The batch quantities of propylene glycol, phenoxyethanol were taken in another SS vessel and mixed well under slow stirring. To it Ivermectin was added under continuous stirring and mixed well till clear solution is formed.

Emulsification:

v. Oil phase was added to the aqueous phase under homogenization. Homogenization was continued for about 30 minutes while maintaining the temperature to 60° to 70° C.

vi. The bulk solution was cooled to the temperature to 45° to 55° C.

Drug Phase Addition:

vii. Drug phase solution was added to the bulk of step vi. The drug phase container was rinsed with part quantity of purified water and added to the bulk phase and homogenized.

Final Mixing:

viii. The bulk solution was cooled to 25° to 30° C. under anchor stirring.

ix. The pH of the bulk solution was adjusted with 10% of NaOH solution under continuous anchor stirring.

Example 2

| No | Ingredients | % w/w 2A | 2B | % w/w 2C | 2D |
|---|---|---|---|---|---|
| 1 | Ivermectin | 0.5-5% | | 0.5-5% | |
| 2 | Propylene Glycol | 1.0-3.0 | 1.0-3.0 | 1.0-3.0 | 1.0-3.0 |
| 3 | Phenoxyethanol | 0.5-2.0 | 0.5-2.0 | 0.5-2.0 | 0.5-2.0 |
| 4 | Glycerol | 2.0-6.0 | 2.0-6.0 | 2.0-6.0 | 2.0-6.0 |
| 5 | Carbomer co-polymer Type-B | 0.10-0.50 | — | 0.10-0.50 | — |
| 6 | Polyacrylamides (Sepineo DERM) | — | 0.50-2.0 | — | 0.50-2.0 |
| 7 | Methylparaben | 0.10.0.30 | 0.10.0.30 | 0.10.0.30 | 0.10.0.30 |
| 8 | Disodium EDTA | 0.03-0.06 | 0.03-0.06 | 0.03-0.06 | 0.03-0.06 |
| 9 | Citric acid monohydrate | 0.03-0.06 | 0.03-0.06 | 0.03-0.06 | 0.03-0.06 |
| 10 | Dimethicone 200 20 cs | 0.2-0.8 | 0.2-0.8 | 0.2-0.8 | 0.2-0.8 |
| 11 | Diethyl sebacate/Dimethyl isosorbide | 2.0-6.0 | 2.0-6.0 | 2.0-6.0 | 2.0-6.0 |
| 12 | Cetyl alcohol | 2.0-6.0 | 2.0-6.0 | 2.0-6.0 | 2.0-6.0 |
| 13 | Stearyl alcohol | 1.5-5.0 | 1.5-5.0 | 1.5-5.0 | 1.5-5.0 |
| 14 | Oleyl alcohol | 1.0-3.0 | 1.0-3.0 | 1.0-3.0 | 1.0-3.0 |
| 15 | Polyethylene glycol ethers of oleyl alcohol (Oleth 20) | 1.5-5.0 | 1.5-5.0 | — | — |
| 16 | Polyethylene glycol ethers of oleyl alcohol (Oleth 2) | 1.0-4.0 | 1.0-4.0 | — | — |
| 17 | Polyethylene glycol ethers of lauryl alcohol (Laureth 23) | — | — | 1.5-5.0 | 1.5-5.0 |
| 18 | Polyethylene glycol ethers of lauryl alcohol (Laureth 4) | — | — | 1.0-4.0 | 1.0-4.0 |
| 19 | Propylparaben | 0.05-0.20 | 0.05-0.20 | 0.05-0.20 | 0.05-0.20 |
| 20 | 10% sodium Hydroxide | q.s. pH | q.s. pH | q.s. pH | q.s. pH |
| 21 | Purified water | q.s. | q.s. | q.s. | q.s. |
| | Total (Topical composition) | 100.00 | 100.00 | 100.00 | 100.00 | q.s.: Quantity sufficient

Manufacturing process: Ivermectin cream was prepared with similar process as mentioned under example-1.

Example 3

| Ingredient | Quantity (% w/w) 3A | 3B | 3C | 3D |
|---|---|---|---|---|
| Active Phase | | | | |
| Ivermectin USP | 1.00 | 1.00 | 1.00 | 1.00 |
| Propylene Glycol USP | 2.00 | 2.00 | 2.00 | 2.00 |
| Phenoxyethanol NF | 1.00 | 1.00 | 1.00 | 1.00 |
| Propylparaben NF | 0.10 | 0.10 | 0.10 | 0.10 |
| Methyl paraben NF | 0.20 | 0.20 | 0.20 | 0.20 |
| Aqueous Phase | | | | |
| Glycerine USP | 4.00 | 4.00 | 4.00 | 4.00 |
| Acrylate alkyl acrylate crosspolymer (Carbomer; Type-B) | — | 0.20 | — | 0.20 |

-continued

| Ingredient | Quantity (% w/w) | | | |
|---|---|---|---|---|
| | 3A | 3B | 3C | 3D |
| Hydroxyethyl Acrylate/ Sodium Dimethyl Acryloyl Taurate Copolymer (Sepineo Derm ™) | 1.00 | — | 1.00 | — |
| Edetate Disodium USP | 0.05 | 0.05 | 0.05 | 0.05 |
| Citric acid monohydrate USP | 0.05 | 0.05 | 0.05 | 0.05 |
| Oil Phase | | | | |
| Dimethicone 200 20 cst IH | 0.50 | 0.50 | 0.50 | 0.50 |
| Cetyl alcohol NF | 3.50 | 3.50 | 3.50 | 3.50 |
| Stearyl alcohol NF | 2.50 | 2.50 | 2.50 | 2.50 |
| Oleyl alcohol NF | 2.00 | 2.00 | 2.00 | 2.00 |
| Polyethylene glycol ethers of oleyl alcohol (Oleth 20) | — | — | 3.60 | 3.00 |
| Polyethylene glycol ethers of oleyl alcohol (Oleth 2) | — | — | 2.40 | 2.00 |
| Polyethylene glycol ethers of lauryl alcohol (Laureth 23) | 2.00 | 2.00 | — | — |
| Polyethylene glycol ethers of lauryl alcohol (Laureth 4) | 2.00 | 2.00 | — | — |
| Isopropyl palmitate NF | 4.00 | 4.00 | 4.00 | 4.00 |
| Sodium Hydroxide NF | Q.S | Q.S | Q.S | Q.S |
| Purified Water USP | QS 100 | QS 100 | QS 100 | QS 100 |
| pH@ | 6.24 | 6.09 | 6.19 | 5.90 |
| Viscosity# | 1.25 P | 1.35 P | 1.82 P | 1.17 P |

@Viscosity was determined using Brookfield CAP 2000+ viscometer at 500 rpm, 30 sec.
pH was measured as such.

Manufacturing Procedure:
Preparation of Aqueous Phase:
i. Weigh and transfer calculated quantity of purified water in SS container. Keep part quantity of purified water for rinsing. Add glycerin and heat to 60° to 70° C. Then add Edetate disodium, citric acid to it under stirring with an overhead stirrer.
ii. Add Sepineo™ derm, Sepineo™ P 600 or Simulgel™ 600 or carbopol or mixture thereof under continuous stirring to above step and mix well.

Preparation of Oil Phase:
iii. Weigh cetyl alcohol, stearyl alcohol, oleyl alcohol, dimethicone, laureth 23, laureth 4, or Oleth 20, Oleth 2 and isopropyl palmitate; transfer in another SS vessel. Heat it to 60° to 70° C. and mix well under slow stirring.

Preparation of Drug Phase:
iv. In another SS vessel, take batch quantity of propylene glycol. To it add phenoxyethanol & stir well. Then add methylparaben, propylparaben and Ivermectin under continuous stirring and mix to dissolve completely until clear solution is formed.

Emulsification:
v. Add oil phase to the aqueous phase under homogenization. Continue homogenization for about 30 minutes maintaining the temperature to 60° to 70° C.
vi. Cool the bulk under homogenization to the temperature to 50° to 55° C.

Drug Phase Addition:
vii. Add drug phase to the bulk of step vi. Rinse the drug phase container with part quantity of purified water kept aside in step i and add it to the bulk phase and homogenize the bulk for 5 minutes.

Final Mixing:
viii. Cool the bulk to 25° to 30° C. under anchor stirring.
viii. Check and adjust the pH of the bulk using 10% of Sodium hydroxide solution under continuous anchor stirring.

Example 4

| No | Name of the Ingredient | Quantity (% w/w) |
|---|---|---|
| | Active Phase | |
| 1 | Ivermectin | 1.00 |
| 2 | Diethylene Glycol Monoethyl Ether | 5.00 |
| 3 | Methylparaben | 0.20 |
| 4 | Propylparaben | 0.10 |
| | Aqueous Phase | |
| 5 | Edetate disodium | 0.05 |
| 6 | Citric acid monohydrate | 0.05 |
| 7 | Glycerin | 4.00 |
| 8 | Carbomer co-polymer Type B | 0.20 |
| | Oil Phase | |
| 9 | Cetyl alcohol | 3.50 |
| 10 | Stearyl alcohol | 2.50 |
| 11 | Dimethicone 200 20 cst | 0.50 |
| 12 | Isopropyl palmitate | 4.00 |
| 13 | Polyoxy 20 cetosteryl ether | 3.00 |
| 14 | Sorbiton monostearate | 2.00 |
| 15 | 10% Sodium Hydroxide | q.s. (pH) |
| 16 | Purified water | q.s. 100% |

Manufacturing process: Ivermectin cream was prepared with similar process as mentioned under example-1.

Stability of ivermectin compositions 1-2 and 5-6 were evaluated by various parameters such as % assay, pH, viscosity and it was found to be stable over a period of 6 months when stored at 40° C. and at 75% relative humidity. The stability data is given below and these results demonstrate the very good chemical stability of the ivermectin in the composition as a function of time.

Stability Data of Ivermectin Cream 1%

| Assay of Ivermectin (% w/w) | | | | |
|---|---|---|---|---|
| | | 40° C./75% RH | | |
| Example | Initial* | 1 M* | 3 M* | 6 M* |
| 1 | 95.00-105.00 | 90.00-110.00 | 90.00-110.00 | 90.00-110.00 |
| 2 | 95.00-105.00 | 90.00-110.00 | 90.00-110.00 | 90.00-110.00 |
| 5 | 95.00-105.00 | 90.00-110.00 | 90.00-110.00 | 90.00-110.00 |
| 6 | 95.00-105.00 | 90.00-110.00 | 90.00-110.00 | 90.00-110.00 |

*Meets Specification

| pH | | | | |
|---|---|---|---|---|
| | | 40° C./75% RH | | |
| Example | Initial | 1 M | 3 M | 6 M |
| 1 | 6.24 | 6.32 | 6.14 | 6.21 |
| 2 | 6.09 | 6.06 | 6.02 | 6.11 |
| 5 | 6.19 | 6.13 | 6.10 | 6.13 |
| 6 | 5.90 | 5.76 | 5.71 | 5.82 |

| | Viscosity (Poise) | | | |
|---|---|---|---|---|
| | | 40° C./75% RH | | |
| Example | Initial | 1 M | 3 M | 6 M |
| 1 | 1.261 | 1.274 | 1.238 | 1.256 |
| 2 | 1.352 | 1.222 | 1.275 | 1.282 |
| 5 | 1.822 | 1.831 | 1.787 | 1.807 |
| 6 | 1.177 | 1.188 | 1.190 | 1.183 |

We claim:

1. A topical pharmaceutical composition comprising: a) about 0.1-5% w/w of ivermectin; b) an oil phase comprising at least one surfactant emulsifier; c) an aqueous phase comprising about 0.1-10% w/w of a gelling agent, wherein the gelling agent is Hydroxyethyl acrylate/sodium acryloyldimethyl taurate copolymer; d) 0.5-10% w/w of a penetration enhancer, wherein the penetration enhancer is diethyleneglycol monoethyl ether; e) optionally one or more pharmaceutically acceptable excipients.

2. The topical pharmaceutical composition according to claim 1, prepared by a process comprising the following steps:
a) Preparing the aqueous phase;
b) Preparing the oil phase;
c) Adding ivermectin into the one or more pharmaceutically acceptable excipient(s) or solvent(s) to form an active phase;
d) Adding the oil phase to the aqueous phase and homogenizing; and
e) Adding the active phase of step-c to the homogenized oil phase and aqueous phase of step-d to obtain a dosage form.

3. The topical pharmaceutical composition according to claim 1, wherein said composition comprises 1% w/w of ivermectin.

4. The topical pharmaceutical composition according to claim 1, wherein said composition further comprises one or more pharmaceutically acceptable additives selected from the group consisting of stabilizers, solubilizers, preserving agents, humidity regulators, pH regulators, osmotic pressure modifiers, antioxidants, emulsifying agents, additional penetration enhancers and solvents.

5. The topical pharmaceutical composition according to claim 4, wherein said one or more additives are selected from the group consisting of glycerol, methyl paraben, propyl paraben, disodium EDTA, citric acid, cetyl alcohol, stearyl alcohol, oleyl alcohol, isopropyl palmitate, esters of sebacic acid, diethyl sebacate, dimethyl isosorbide, dimethicone, propylene glycol, phenoxyethanol, sorbitan monostearate, polyoxyl 20 cetostearyl ether and sodium hydroxide.

6. The topical pharmaceutical composition according to claim 1, wherein said composition is in the form of cream, gel, foam or lotion.

7. The topical pharmaceutical composition according to claim 1 wherein said oil phase further comprises fatty substances selected from the group consisting of cetyl alcohol, stearyl alcohol, oleyl alcohol and dimethicone.

8. A method of treatment of rosacea comprising topically applying the composition of claim 1 onto the affected skin area of an individual in need of such treatment.

9. The topical pharmaceutical composition according to claim 1, wherein said composition has a pH in the range of about 4.5-7.5, viscosity in the range of about 0.1-5 poise and wherein said composition exhibits stability over a period of at least 6 months when stored at 40° C. and at 75% Relative humidity.

10. The topical pharmaceutical composition of claim 9 wherein said composition has a pH in the range of about 5.5-6.5, and viscosity in the range of about 1.2-2 poise.

11. A topical pharmaceutical composition according to claim 1 consisting of: a) about 0.1-5% w/w of ivermectin; b) an oil phase comprising at least one surfactant emulsifier selected from 2-10% w/w of Polyethylene glycol ethers of oleyl or lauryl alcohol or sorbitan fatty acid mono ester or Polyoxyl 20 Cetostearyl ether or mixtures thereof; c) an aqueous phase comprising 0.1-10% w/w of a gelling agent, wherein the gelling agent is Hydroxyethyl acrylate/sodium acryloyldimethyl taurate copolymer; d) 0.5-10% w/w of a penetration enhancer, wherein the penetration enhancer is diethylene glycol monoethyl ether; and e) optionally one or more pharmaceutically acceptable excipients.

12. A topical pharmaceutical composition according to claim 1 consisting of Ivermectin USP 0.1-5.00% w/w; Glycerin USP 1.5-10% w/w; Hydroxyethyl acrylate/sodium acryloyldimethyl taurate copolymer, 0.5-5% w/w; Edetate disodium USP 0.05% w/w; Citric acid monohydrate USP 0.05% w/w; Isopropyl palmitate 0.5-10.00% w/w; Cetyl alcohol 2.0-6.0% w/w; Stearyl alcohol 1.5-5.0% w/w; Polyoxyl 20 cetostearyl ether 3-6% w/w; Laureth 4 1.0-4.0% w/w; Methylparaben 0.20% w/w; Propylparaben 0.10% w/w; Diethylene glycol Monoethyl ether 0.5-10% w/w; and Purified water Q.S 100.00% w/w.

13. A topical pharmaceutical composition according to claim 1 consisting of Ivermectin USP 1.00% w/w; Glycerin USP 4.00% w/w; Hydroxyethyl acrylate/sodium acryloyldimethyl taurate copolymer, 2.00% w/w; Edetate disodium USP 0.05% w/w; Citric acid monohydrate USP 0.05% w/w; Isopropyl palmitate 4.00% w/w; Cetyl alcohol 3.50% w/w; Stearyl alcohol 2.50% w/w; Polyoxyl 20 cetostearyl ether 4.00% w/w; Laureth 4 4.00% w/w; Methylparaben 0.20% w/w; Propylparaben 0.10% w/w; Diethylene glycol Monoethyl ether 5.00% w/w; and Purified water Q.S 100.00% w/w.

14. A topical pharmaceutical composition comprising: a) about 0.1-5% w/w of ivermectin; b) an oil phase comprising at least one surfactant emulsifier selected from polyethylene glycol ethers of fatty alcohol or sorbitan fatty acid mono ester or Polyoxyl 20 Cetostearyl ether or mixtures thereof; c) an aqueous phase comprising a gelling agent, wherein the gelling agent is Hydroxyethyl acrylate/sodium acryloyldimethyl taurate copolymer; d) 0.5-10% w/w of a penetration enhancer, wherein the penetration enhancer is diethyleneglycol monoethyl ether; e) optionally one or more pharmaceutically acceptable excipients.

15. The topical pharmaceutical composition according to claim 14, wherein said composition contains 0.1-5% w/w of said ivermectin, and 10-20% w/w of said oil phase.

16. The topical pharmaceutical composition according to claim 15, wherein said composition contains 0.5-2% w/w of said ivermectin, and 10-20% w/w of said oil phase.

17. The topical pharmaceutical composition according to claim 14, wherein said gelling agent is present in the amount of 0.1-10% w/w.

18. A topical pharmaceutical composition comprising: a) about 0.1-5% w/w of ivermectin; b) an oil phase comprising at least one surfactant emulsifier selected from 2-10% w/w of Polyethylene glycol ethers of oleyl or lauryl alcohol or sorbitan fatty acid mono ester or Polyoxyl 20 Cetostearyl ether or mixtures thereof; c) an aqueous phase comprising 0.5-5% w/w of a gelling agent, wherein the gelling agent is Hydroxyethyl acrylate/sodium acryloyldimethyl taurate copolymer; d) 0.5-10% w/w of a penetration enhancer, wherein the penetration enhancer is diethyleneglycol monoethyl ether; e) optionally one or more pharmaceutically acceptable excipients.

\* \* \* \* \*